United States Patent
Hwang et al.

(10) Patent No.: US 11,147,798 B2
(45) Date of Patent: Oct. 19, 2021

(54) USE OF CARBAMATE COMPOUND FOR PREVENTION, ALLEVIATION, OR TREATMENT OF DEMYELINATING DISEASE

(71) Applicant: SK BIOPHARMACEUTICALS CO., LTD., Gyeonggi-do (KR)

(72) Inventors: Sun Gwan Hwang, Gyeonggi-do (KR); Jihye Kim, Gyeonggi-do (KR); Jimok Yoon, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 204 days.

(21) Appl. No.: 16/468,985

(22) PCT Filed: Dec. 14, 2017

(86) PCT No.: PCT/KR2017/014737
§ 371 (c)(1),
(2) Date: Jun. 12, 2019

(87) PCT Pub. No.: WO2018/111006
PCT Pub. Date: Jun. 21, 2018

(65) Prior Publication Data
US 2019/0314338 A1    Oct. 17, 2019

(30) Foreign Application Priority Data
Dec. 14, 2016 (KR) .................. 10-2016-0170226

(51) Int. Cl.
*A61K 31/41* (2006.01)
*A61P 27/02* (2006.01)
*A61P 21/00* (2006.01)

(52) U.S. Cl.
CPC .............. *A61K 31/41* (2013.01); *A61P 21/00* (2018.01); *A61P 27/02* (2018.01)

(58) Field of Classification Search
CPC ........... A61K 31/41; A61P 27/02; A61P 21/00
See application file for complete search history.

(56) References Cited

U.S. PATENT DOCUMENTS

2016/0355488 A1    12/2016    Davies et al.

FOREIGN PATENT DOCUMENTS

| EP | 1383489 B1 | 5/2007 |
| JP | S6100011 A | 1/1986 |
| KR | 10-2001-0022877 A | 3/2001 |
| KR | 10-2008-0005437 A | 1/2008 |
| WO | WO-2006/112685 A1 | 10/2006 |
| WO | WO-2007/092681 A2 | 8/2007 |
| WO | WO-2010/150946 A1 | 12/2010 |
| WO | WO-2011/046380 A2 | 4/2011 |
| WO | WO-2017/200317 A1 | 11/2017 |

OTHER PUBLICATIONS

Extended European Search Report from corresponding European Patent Application No. 17880336.7, dated May 18, 2020.
Bailer, M., et al.; "Progress report on new antiepileptic drugs: A summary of the Tenth Eilat Conference (EILAT X)", Epilepsy Research (2010), 92, pp. 89-124.
International Search Report from corresponding PCT Application No. PCT/KR2017/014737, dated Mar. 27, 2018, with English translation.
S Love, Demyelinating disease, J. Clin. Pathol., 2006, 59, 1151-1159).
TA Pivneva, Mechanisms Underlying the Process of Demyelination in Multiple Sclerosis, Neurophysiology, 2009, 41, 365-373).
CA Opere, KK O'Brien, MH Elhaj, Optic Neuritis: A Brief Review, US Pharm, 2016, 41(1), 35-40.
Cris S Constantinescu, Nasr Farooqi, Kate O'Brien, Bruno Gran, Experimental autoimmune encephalomyelitis (EAE) as a model for multiple sclerosis (MS), Br. J. Pharmacol., 2011, 164, 1079-1106.
B Gran, G-X Zhang, S Yu, J L i, X H C hen, E S Ventura, M Kamoun, A Rostami, J. Immunol., 2002, 169, 7104-7110.

*Primary Examiner* — Yong S. Chong
(74) *Attorney, Agent, or Firm* — Harness, Dickey & Pierce, P.L.C.

(57) ABSTRACT

The present invention relates to a use for preventing, alleviating or treating a demyelinating disease by administering a pharmaceutical composition containing a carbamate compound of chemical formula 1.

9 Claims, 2 Drawing Sheets

USE OF CARBAMATE COMPOUND FOR PREVENTION, ALLEVIATION, OR TREATMENT OF DEMYELINATING DISEASE

CROSS-REFERENCE TO RELATED APPLICATIONS

This application is a national phase application of PCT Application No. PCT/KR2017/014737, filed on Dec. 14, 2017, which claims the benefit and priority to Korean Patent Application No. 10-2016-0170226, filed on Dec. 14, 2016. The entire disclosures of the applications identified in this paragraph are incorporated herein by references.

FIELD

The present invention relates to use of a carbamate compound of the following Formula 1 for the purpose of preventing, alleviating or treating demyelinating diseases by administering a pharmaceutical composition comprising said carbamate compound:

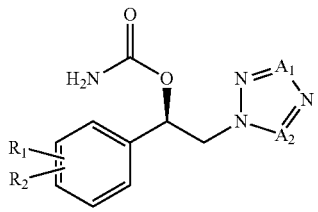

[Formula 1]

wherein,
$R_1$, $R_2$, $A_1$ and $A_2$ are as defined herein.

BACKGROUND

The neuron axon is surrounded by myelin except for the node of Ranvier. Schwann cells form myelin in the peripheral nervous system, whereas oligodendrocytes form myelin in the central nervous system. The myelin protects and supports the axons and has an electric shielding function, which contributes to nerve conduction. The conduction velocity is proportional to the distance between the nodes of Ranvier or the thickness of the myelin. Demyelinating disease refers to a case in which myelin is damaged without a significant injury to nerve cell itself or an axon, and may occur in both the peripheral nervous system and the central nervous system. Pathological features typical of demyelinating diseases include inflammation, demyelination, and loss of axons and oligodendrocytes. In addition to the myelin-axonal dissociation phenomenon which is characterized by destruction of only myelin without significant loss of axons, demyelinating diseases show a multiple demyelinating plaque that is mainly distributed around the blood vessels and accompanied by infiltration of inflammatory cells. Additional characteristic features include multiple inflammation, demyelination and glial scarring. These lesions may occur anywhere in the central nervous system, but they occur most frequently in the periventricular white matter, the optic nerve and the optic nerve crossing, the spinal cord, the cerebellum, the cerebellar peduncle, the corpus callosum and the like (S Love, Demyelinating disease, J. Clin. Pathol., 2006, 59, 1151-1159).

Demyelinating disease may include Multiple sclerosis (MS), optic neuritis, Devic's syndrome, Neuromyelitis optica (NMO), Acute disseminated encephalomyelitis (ADEM), Acute transverse myelitis (ATM) and Central pontine myelinolysis.

Multiple sclerosis (MS), the most common disease of central nervous system demyelinating diseases, is an immune-mediated disease characterized by gradual decline and finally permanent disabling of motor neurons and sensory functions due to chronic inflammatory demyelination of oligodendrocytes. While patients in the early stage may recover well without disability, multiple sclerosis is a chronic inflammatory disease with various clinical features and the repeated recovery and recurrence (relapse), which result in disability (TA Pivneva, Mechanisms Underlying the Process of Demyelination in Multiple Sclerosis, Neurophysiology, 2009, 41, 365-373).

The cause of multiple sclerosis has not yet been elucidated, but multiple sclerosis is thought to be a type of autoimmune disease that occurs when the immunological control function in genetically susceptible individuals is broken by certain environmental factors.

This causes loss of axons in the early stages of the disease, and such loss occurs extensively over time, resulting in permanent progressive nerve damage, and moreover frequently development of a subsequent severe disability. Symptoms associated with the disease include fatigue, stiffness, ataxia, weakness, bladder and bowel disturbance, sexual dysfunction, pain, tremors, seizure findings, visual impairment, psychological problems and cognitive dysfunction.

Among the above-enumerated symptoms of multiple sclerosis, some will be described in more detail as follows.

Relapsing remitting multiple sclerosis (RR-MS) occurs over a period of 1 to 2 weeks and is usually accompanied by dissociative movement, sensory, cerebellar or visual paralysis that is relieved over a period of 1 to 2 months. Some patients have disabilities in each episode but remain clinically stable between relapses. Symptoms are aggravated (relapse phase) and then relieved (remission phase), and this occurs repeatedly, and it is difficult to predict when relapse will happen. During relapse, symptoms that have already appeared may worsen and new symptoms may appear. However, symptoms completely or partially disappear during remission. As such, relapse (recurrence) and remission are clearly distinguished and proceed in a stepwise manner.

Secondary progressive multiple sclerosis (SP-MS) refers to a case in which relapsing remitting multiple sclerosis was first initiated and secondarily progressed into irreversible disorder. The disease is characterized by the period of recurrence, the period of remission of symptoms and the period of stabilization. As the disease progresses, the nervous function gradually disappears.

Primary progressive multiple sclerosis (PP-MS) occurs in about 15% of patients with multiple sclerosis, in which symptoms slowly progress and slowly worsen. The remission phase and the relapse phase are not clearly distinguished, and although there is a difference in the rate of progression, the function gradually disappears as the disease progresses from its onset without any recurrence or remission.

Progressive relapsing multiple sclerosis (PR-MS) occurs in about 6% to 10% of patients with multiple sclerosis and they can fully recover or partially recover after a sudden acute relapse. However, differently from relapsing remitting multiple sclerosis, this disease is characterized by a continuous progression of the disease between relapse and relapse.

Diagnosis of multiple sclerosis can be monitored by two scans including magnetic resonance imaging (MRI) of the brain, accumulation of disorders, recurrence rate and recurrence severity according to the 2010 updated McDonald's criteria. Additional tests include magnetic resonance spectroscopy (MR spectroscopy), cerebrospinal fluid testing and evoked potentials testing. In addition, studies have been conducted on the use of biomarkers by directly measuring an antibody to myelin in the serum of a patient.

Treatment for multiple sclerosis can be divided into acute phase treatment, long-term disease modifying therapy and symptomatic therapy.

Acute phase treatment is generally done by administration of high dose corticosteroids intravenously for several days.

In the relapse phase of multiple sclerosis, long-term disease relief therapy is applied to reduce or prevent the progression of neurodegeneration. Interferon beta 1-a (Avonex® and Rebif®), Interferon beta 1-b (Betaseron®), Glatiramer acetate (Copaxone®), Mitoxantrone (Novantrone®), Natalizumab (Tysabri®), Fingolimod (Gilenya®), etc. are used.

However, current therapies for multiple sclerosis are only partially effective for symptom relief, and in most cases, despite the anti-inflammatory and immunosuppressive treatments, they only provide a short delay in disease progression and do not achieve a satisfactory level of efficacy or have side effects. Hence, current therapies still have limitations on their use.

Another example of demyelinating diseases is optic neuritis. Optic neuritis is a disease in which demyelination occurs in the optic nerve due to inflammation induced by various causes, and even further damage to nerve cells occurs. The optic nerve has the function of transmitting visual information from the retina to the brain. Information is transferred by the transfer of the action potential through the axon of the retinal ganglion cell. When optic neuritis occurs, the myelin necessary for efficient conduction of the action potential is damaged, causing symptoms such as eye pain, vision loss, loss of color vision and blindness.

Depending on the etiology, optic neuritis can be divided into two main types: typical optic neuritis, which is associated with multiple sclerosis, and atypical optic neuritis, which is not associated with multiple sclerosis. Typical optic neuritis occurs predominantly in white people (Caucasian) in ages of 20 to 55 and occurs more frequently in women. On the other hand, atypical optic neuritis occurs in all races to people younger than 12 or over 50 (C A Opere, K K O'Brien, M H Elhaj, Optic Neuritis: A Brief Review, US Pharm, 2016, 41(1), 35-40).

Treatment of typical optic neuritis aims to prevent inflammation, increase speed of recovery and restore vision in the short term. In the long term, it aims to prevent recurrence of optic neuritis, and to prevent, delay and alleviate subsequent multiple sclerosis. Commonly used therapies include high doses of Corticosteroids, Interferon beta and Glatiramer acetate. Plasma exchange may be used in patients who do not respond to steroid therapy. Atypical optic neuritis is caused by various factors such as infection, compressive tumor, nutrition, toxicity or drug, and thus appropriate treatment is used depending on the type of the cause. The currently used therapies for optic neuritis can slow the onset rate and recurrence frequency by controlling inflammation and immune response. However, as they cannot ameliorate the nerve damage that has already occurred, there is a limit to the fundamental treatment of the disease. These therapies also have side effects such as weight gain, mood swings, depression, facial flushing, abdominal pain and insomnia, which limits their use.

DISCLOSURE

Problem to be Solved

The present invention is intended to provide a method for the prevention, alleviation or treatment of demyelinating diseases.

The present invention is also intended to provide the use of a carbamate compound of the following Formula 1, or a pharmaceutically acceptable salt, solvate or hydrate thereof, for the prevention, alleviation or treatment of demyelinating diseases:

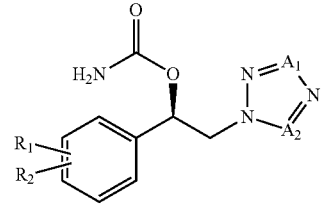

[Formula 1]

wherein,
$R_1$, $R_2$, $A_1$ and $A_2$ are as defined herein.

Technical Solution to the Problem

The present invention provides a medicament for the prevention, alleviation or treatment of demyelinating diseases, comprising a therapeutically effective amount of a carbamate compound of the following Formula 1, or a pharmaceutically acceptable salt, solvate or hydrate thereof:

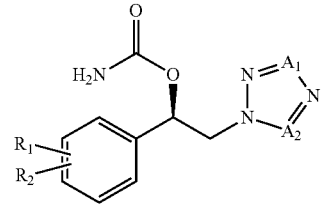

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

In addition, the present invention provides a pharmaceutical composition for the prevention, alleviation or treatment of demyelinating diseases, comprising a therapeutically effective amount of the carbamate compounds of the above Formula 1, or a pharmaceutically acceptable salt, solvate or hydrate thereof, and further one or more of a pharmaceutically acceptable carrier.

In addition, the present invention provides a method for preventing, alleviating or treating demyelinating diseases in a subject, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention, alleviation or treatment of demyelinating diseases, or for the improvement of symptoms associated with demyelinating diseases.

In one embodiment of the present invention, in the above Formula 1, $R_1$ and $R_2$ are each independently selected from the group consisting of hydrogen, halogen and $C_1$-$C_8$ alkyl.

In one embodiment of the present invention, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

[Formula 2]

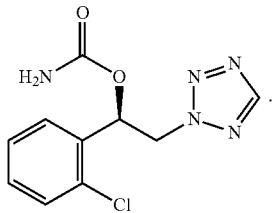

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of demyelinating diseases.

Demyelinating diseases are associated with damage of myelin of nerves such as destruction or removal of myelin of nerves.

According to one embodiment of the present invention, the demyelinating diseases may be demyelinating diseases in the central nervous system or the peripheral nervous system. The demyelinating diseases include Multiple sclerosis, Optic neuritis, Devic's disease, Other inflammatory demyelinating diseases, Neuromyelitis optica, Chronic relapsing isolated optic neuropathy (CRION), Acute disseminated encephalomyelitis, Post-infectious encephalomyelitis, Acute hemorrhagic leukoencephalomyelitis (AHEM), Balo's concentric sclerosis, Schilder's disease, Marburg-type multiple sclerosis, Tumefactive multiple sclerosis, Central pontine myelinolysis, Tabes *dorsalis*, Leukoencephalopathies, Progressive multifocal leukoencephalopathy, Leukodystrophies, Adrenoleukodystrophy, Adrenomyeloneuropathy, Krabbe's disease, Transverse myelitis, Guillain-Barré syndrome, Chronic inflammatory demyelinating polyneuropathy, Anti-MAG peripheral neuropathy, Charcot-Marie-Tooth disease, Progressive inflammatory neuropathy and the like.

Other examples of demyelinating diseases include Leber's hereditary optic atrophy and related mitochondrial disorders, HTLV (human T-cell lymphotrophic virus)-associated myelopathy (HTLV-associated myelopathy), demyelinating diseases resulting from local injury, ischemia, toxic agents or metabolic disorders, Lhermitte syndrome (Barber's chair syndrome), Uhthoff symptom and Viral demyelinating diseases.

The compounds of the above Formula 1 can be used for the prevention, alleviation or treatment of multiple sclerosis.

The compounds of the above Formula 1 can be used for the prevention, alleviation or treatment of optic neuritis. Many patients with multiple sclerosis develop optic neuritis at an early stage, which causes damage to the optic nerve.

According to one embodiment of the present invention, the multiple sclerosis may be one or more selected from the group consisting of Clinically isolated syndrome (CIS), Radiologically isolated syndrome (RIS), Clinically definite multiple sclerosis (CDMS), Relapsing remitting multiple sclerosis (RR-MS), Secondary progressive multiple sclerosis (SP-MS), Primary progressive multiple sclerosis (PP-MS) and Progressive relapsing multiple sclerosis (PR-MS).

An Experimental Autoimmune Encephalomyelitis (EAE) model may be used for the measurement of the activity of the compounds of Formulas 1 and 2 for multiple sclerosis as demyelinating diseases. Experimental Autoimmune Encephalomyelitis is an inflammatory autoimmune demyelinating disease induced by injecting a myelin basic protein into experimental animals. Experimental Autoimmune Encephalomyelitis (EAE) model is a representative model for neurological diseases caused by brain inflammation and inflammatory demyelination phenomenon. It is used to find new drug candidates for treatment of multiple sclerosis and Acute disseminated encephalomyelitis (ADEM). EAE models can be used to study demyelinating diseases such as multiple sclerosis, since chronic recurrent EAE in animals and multiple sclerosis in humans are similar in clinical symptoms or histopathological findings (Cris S Constantinescu, Nasr Farooqi, Kate O'Brien, Bruno Gran, Experimental autoimmune encephalomyelitis (EAE) as a model for multiple sclerosis (MS), Br. J. Pharmacol., 2011, 164, 1079-1106).

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above. The therapeutically effective amount of the compounds of the present invention is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated as a plain tablet (uncoated tablet) or such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, preferably 50 to 300 mg, more preferably 50 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat and prevent demyelinating diseases, especially multiple sclerosis or optic neuritis.

DETAILED DESCRIPTION

Figure 1:
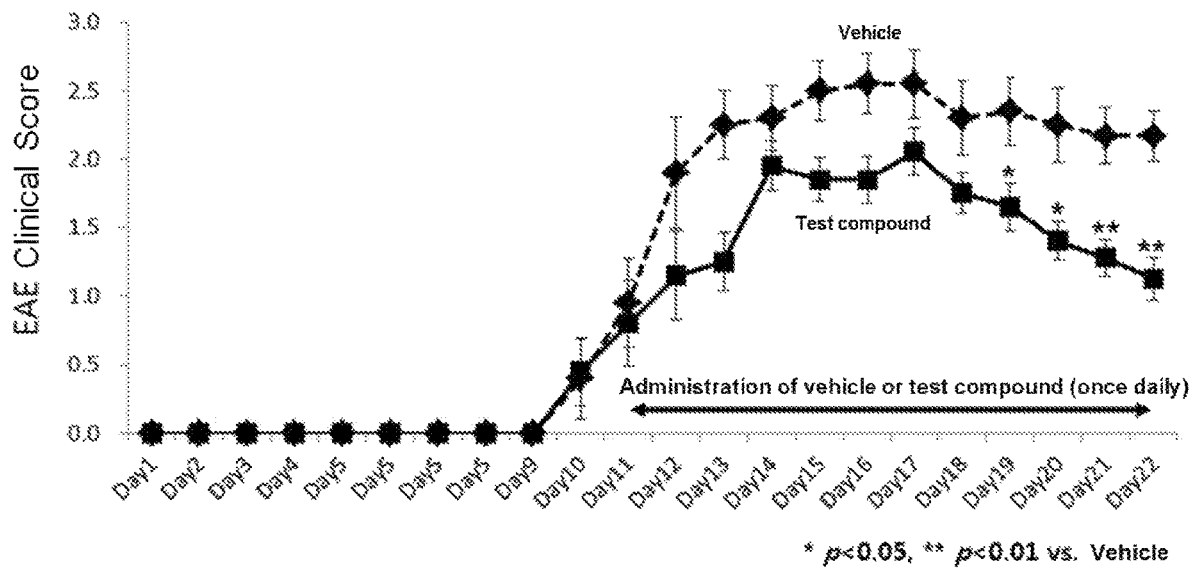
FIG. 1 is a graph showing the results of a systematic motor symptom alleviation experiment in an Experimental Autoimmune Encephalomyelitis (EAE) model.

Hereinafter, the present invention will be explained in more detail through working examples. However, the following working examples are only intended to illustrate one or more embodiments and are not intended to limit the scope of the invention.

Preparation Example: Synthesis of carbamic acid (R)-1-(2-chlorophenyl)-2-tetrazol-2-yl)ethyl ester Carbamic acid (R)-1-(2-chlorophenyl)-2-tetrazol-2-yl) ethyl ester (the compound of Formula 2, hereinafter referred to as "the test compound") was prepared according to the method described in Preparation Example 50 of PCT Publication No. WO 2010/150946.

Example 1: Systemic Motor Symptom Alleviation Effect in an Experimental Autoimmune Encephalomyelitis (EAE) Model Experimental Animals For this experiment, male C57BL/6 mice were purchased from Orient Bio, Inc. of Korea. The mice were placed in a wire mesh cage under conditions of ambient temperature of 20 to 24° C., relative humidity of 55 to 75%, an automatically controlled light-and-darkness cycle of 12 hours and free access to feed (purchased from Agri Brands Purina Korea, Inc.) and water. The mice were housed and maintained in accordance with the Laboratory Animal Care Standards of the Institutional Animal Care and Use Committee (IACUC). After about one week of stabilization, mice weighing 18 to 23 g were used in the experiment.

Preparation of EAE-Inducing Samples

To 100 mg of *Mycobacterium tuberculosis* H37RA (killed and desiccated; Difco, 231141, USA) which had been well triturated in mortar, was mixed 10 ml of Incomplete Freund's adjuvant (IFA; Difco, 263910, USA) to prepare 10 mg/ml of Complete Freund's adjuvant (CFA) storage solution, followed by refrigeration at 4° C. Myelin oligodendrocyte glycoprotein (MOG35-55; Peptron, Korea) was diluted with PBS (phosphate-buffered saline; Gibco, 10010, USA) to a final concentration of 2 mg/ml and stored at −20° C. (MOG35-55 storage solution).

In order to prepare EAE-inducing samples for administration to mice, 1 ml of CFA storage solution diluted to 2 mg/ml with IFA solution and 1 ml of $MOG_{35-55}$ storage solution were each put into different syringes, and a 3-way stopcock was used to mix them well at a ratio of 1:1 for over 10 minutes such that air bubbles did not form inside to obtain an emulsion solution having a final concentration of 1 mg/ml.

50 μg of PTX (pertussis toxin, PTX; Sigma, P7208, USA) was dissolved in 500 μl of PBS to prepare 100 μg/ml of pertussis toxin (PTX) storage solution, followed by registration at 4° C. In the experiment, the PTX storage solution was diluted 50 times with PBS and used.

EAE-Inducing Samples/Drug Administration and Clinical Symptom Observation

On the first day of the experiment (Day-1), the EAE-inducing sample solution was administered to mice by subcutaneous injection at 200 μl per mouse. On the same day (Day-1) and two days later (Day-3), 200 μl of PTX solution was intraperitoneally administered to mice twice. In addition, the mice were observed once every day to check whether the EAE-related clinical symptoms were exhibited, and evaluated by EAE clinical score.

The EAE clinical score is as follows.
0.0: normal gait
0.5: normal gait, partially limp tail, tip of tail droops
1.0: normal gait, paralyzed limp tail, tail droops
1.5: uncoordinated gait, limp tail, hind limb paresis
2.0: one hind limb dragging, one hind limb paralyzed
2.5: both hind limb dragging, both hind limbs paralyzed
3.0: forelimb weakness, forelimb reflex after pinching
3.5: one forelimb paralyzed, loss of movement
4.0: both forelimb paralyzed, loss of movement
4.5: moribund, altered breathing
5.0: death From Day-11, on which the EAE clinical score was observed to be 0.5 or more, the test compound dissolved in 30% polyethylene glycol 400 (Sigma, USA) was administered to mice at a dose of 10 ml/kg, in a volume of 10 ml per body weight of a mouse, orally once a day, and changes in the EAE clinical score were observed.

Statistical Analysis

All data were expressed as mean±SEM. The EAE clinical scores in the group treated with the test compound were compared to those in the negative control vehicle group by date. Statistical analysis was performed using GraphPad Prism (ver. 4.0) program, and the differences between the two groups were analyzed by Student's t-test.

Experiment Results

The EAE clinical score changes by day in the vehicle group as a negative control group and the test compound treated group are shown in Table 1 and FIG. 1. The EAE-related clinical symptoms began to be observed on the 9th day after treatment with EAE-inducing sample (Day-10), and the vehicle and the test compound were administered from Day-11 once daily. As a result, the vehicle group showed clinical symptoms of the highest level of 2.6±0.8 on Day-17, and the test compound treated group showed clinical symptoms in the degree of 2.1±0.6 on Day-17. The test compound treated group showed significant inhibition of EAE clinical symptoms compared to the vehicle group on Day-19 to Day-22, indicating that the test compound exhibited a significant efficacy in the EAE model, a representative animal model of multiple sclerosis and demyelinating diseases.

TABLE 1

EAE clinical score change table

| Experiment day | Vehicle | Test compound | Statistical significance (vs. vehicle) |
| --- | --- | --- | --- |
| Day-1~Day-9 | 0.0 ± 0.0 | 0.0 ± 0.0 | None |
| Day-10 | 0.4 ± 1.0 | 0.5 ± 0.8 | None |
| Day-11 | 1.0 ± 1.1 | 0.8 ± 1.0 | None |
| Day-12 | 1.9 ± 1.3 | 1.2 ± 1.1 | None |
| Day-13 | 2.3 ± 0.8 | 1.3 ± 0.7 | None |
| Day-14 | 2.3 ± 0.8 | 2.0 ± 0.6 | None |
| Day-15 | 2.5 ± 0.7 | 1.9 ± 0.5 | None |
| Day-16 | 2.6 ± 0.7 | 1.9 ± 0.6 | None |
| Day-17 | 2.6 ± 0.8 | 2.1 ± 0.6 | None |
| Day-18 | 2.3 ± 0.9 | 1.8 ± 0.5 | None |
| Day-19 | 2.4 ± 0.8 | 1.7 ± 0.6 | $p < 0.05$ |
| Day-20 | 2.3 ± 0.9 | 1.4 ± 0.5 | $p < 0.05$ |
| Day-21 | 2.2 ± 0.7 | 1.3 ± 0.4 | $p < 0.01$ |
| Day-22 | 2.2 ± 0.6 | 1.1 ± 0.5 | $p < 0.01$ |

Example 2: Optic Nerve Damage Alleviation Effect in an Experimental Autoimmune Encephalomyelitis (EAE) Model Experimental Animals For this experiment, female C57BL/6 mice were purchased from Janvier Labs of France and were maintained under conditions of temperature (22±1° C.), a light-and-darkness cycle of 12 hours and free access to water and food according to the protocol approved and investigated by the Animal Experiment Committee of Finland. All animals were kept isolated for a week after purchase and had time to adapt to the kennel. 11-week-old animals were used in the experiment. According to the criteria of the Animal Experiment Committee of Finland, in the case of a weight loss of 20% or more compared to the starting point, a degree of disease progression (clinical score) of 4 or more, or a failure in the righting reflex test in clinical score of 3, the experiment was stopped and animals were sacrificed for humanitarian purposes.

EAE Induction

To induce EAE, an inoculum was purchased from Hooke Laboratories of the United States: the inoculum contains 100 μg of MOG35-55 peptide and 200 μg of heat-inactivated *Mycobacterium tuberculosis*, both dissolved in 100 μl of mineral oil. 100 μl of the inoculum was injected subcutaneously into both high and low parts of the back of mice. 100 μl pertussis toxin was injected into the peritoneum of the mice twice, two hours after inoculation and after 24 hours.

Observation of Clinical Symptoms by EAE

EAE-induced mice were observed daily, and the progression of the disease was measured using the following criteria (B Gran, G-X Zhang, S Yu, J Li, X H Chen, E S Ventura, M Kamoun, A Rostami, J. Immunol., 2002, 169, 7104-7110).

0=No disease
0.5=Partial tail weakness
1.0=Complete tail paralysis
1.5=Flaccid tail and abnormal gait (waddling gait)
2.0=Flaccid tail and clear weakness of hind limbs
2.5=Partial paralysis in one hind limb
3.0=Complete paralysis in both hind limbs
4.0=Complete paralysis in both hind limbs and weakness in forelimbs (requires euthanasia)
5.0=Complete paralysis in all limbs, moribund, death (requires euthanasia)

Preparation and Administration of Compound

The test compound was dissolved in distilled water containing 30% polyethylene glycol 400 (PEG 400) and treated with an ultrasonic sonicator for 30 minutes. The dissolved compound (20 mg/kg or 30 mg/kg) or vehicle was injected into the peritoneum once daily from the 12th day after EAE induction.

Measurement of Pattern Retinal Conduction (pERG)

Pattern retinal conduction was measured two days before and 28 days after EAE induction. A drop of oxybuprocaine was placed on the cornea for partial anesthesia, and the mice were placed on a rodent test bench that maintained the body temperature at approximately 37° C. After performing the test, the results were analyzed using Matlab software (MathWorks, Natick, Mass.).

Animal Sacrifice and Tissue Collecting

When the experiment was terminated or when the time of sacrifice for humanitarian purposes was reached, the mice were sacrificed by cardiac perfusion using a tissue fixative, and the eye and optic nerve were removed for further analysis.

Morphological Assessment of Retinal Whole Mount

The retinal whole mount samples were extracted from both eyes and stained with antibodies of RBPMS (RNA binding protein with multiple splicing) and Brn3a (brain-specific homeobox/POU domain protein 3A) which are retinal ganglion cell markers, followed by analyzation in a stereological manner (Stereo Investigator, MicroBrightfield, VT, USA).

Statistical Analysis

Quantitative data were graphed (plotted) and analyzed using Prism software version 7 (GraphPad Software Inc. La Jolla, Calif.), the data were expressed as mean±standard deviation or standard error of mean. Comparisons with the vehicle group were analyzed using a t-test, and when the significance (p value) was less than 0.05, it was judged as a statistically significant difference.

Experiment Results

1) Pattern Retinal Conduction Amplitude (pERG Amplitude)

Figure 2:
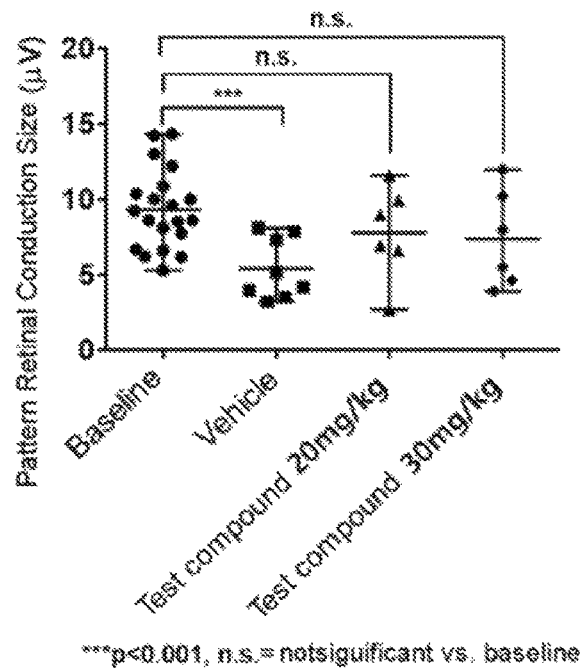
FIG. 2 is a graph showing the results of measuring pattern retinal conduction, which is one of the indicators of functional vision, in an Experimental Autoimmune Encephalomyelitis (EAE) model.

The measurement results of the pattern retinal conduction in the vehicle group as a negative control group and in the compound treatment group are shown in Table 2 and FIG. 2. The amplitude of pattern retinal conduction was reduced by about 40% in the vehicle group compared to the baseline measured two days before EAE-inducing sample treatment (t-test, ***$p<0.001$). In contrast, in the treatment group treated with 20 mg/kg or 30 mg/kg of the test compound, no significant difference was found compared to the baseline. This suggests that the test compound has a tendency to protect the functional vision of the EAE animal model.

TABLE 2

Pattern retinal conduction amplitude (pERG amplitude) measured values

| Treatment group | Baseline | Vehicle | Test compound 20 mg/kg | Test compound 30 mg/kg |
| --- | --- | --- | --- | --- |
| Mean ± SEM | 9.34 ± 0.5866 | 5.435 ± 0.7171 | 7.803 ± 1.268 | 7.378 ± 1.324 |

TABLE 2-continued

Pattern retinal conduction amplitude (pERG amplitude) measured values

| Treatment group | Baseline | Vehicle | Test compound 20 mg/kg | Test compound 30 mg/kg |
|---|---|---|---|---|
| Statistical significance (vs. Baseline) | | ***p < 0.001 | None | None |

2) Number of Retinal Ganglion Cells

Figure 3A:
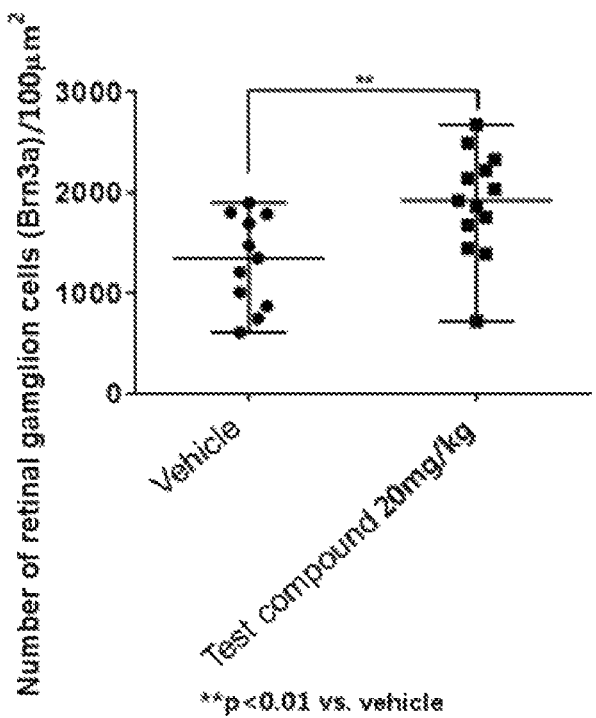
FIGS. 3A and 3B show the results of measuring the number of retinal ganglion cells per unit area in an Experimental Autoimmune Encephalomyelitis (EAE) model, using Brn3a (FIG. 3A) and RBPMS (FIG. 3B) as retinal ganglion cell markers to examine the degree of protection of the optic nerve.
Figure 3B:
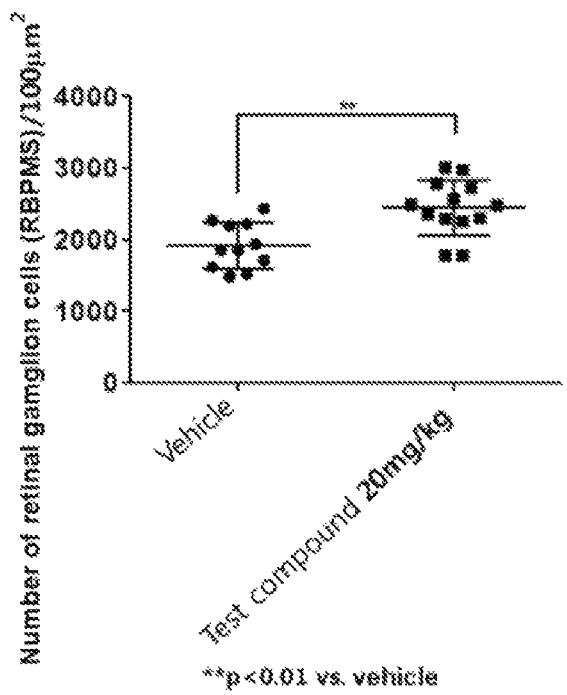

The measurement results of the number of retinal ganglion cells per unit area in the vehicle group as the negative control group and in the compound treatment group are shown in Table 3 and FIG. 3. A larger number of retinal ganglion cells per unit area were observed in the group treated with 20 mg/kg of the test compound compared to the vehicle group in EAE-induced animals. This means that the test compound showed a significant efficacy on the protection of the retinal ganglion cells of the EAE animal model.

TABLE 3

Number of retinal ganglion cells per unit area

| Treatment group | Brn3a | | RBPMS | |
|---|---|---|---|---|
| | Vehicle | Test compound 20 mg/kg | Vehicle | Test compound 20 mg/kg |
| | 1689.82111 | 1389.43278 | 2194.48371 | 2291.69805 |
| | 1205.24606 | 1918.969766 | 1851.58626 | 2567.37062 |
| | 1472.22518 | 2675.372857 | 1851.12316 | 3005.11983 |
| | 606.640405 | 1750.912472 | 1614.33127 | 2250.60258 |
| | 1801.89007 | 1442.818497 | 2431.17226 | 1777.88991 |
| | 1895.57712 | 2138.596922 | 1937.38139 | 2976.21405 |
| | 747.713011 | 719.985283 | 1484.84161 | 1780.68542 |
| | 1345.61213 | 2220.629888 | 2218.24485 | 2296.67886 |
| | 1785.76248 | 1858.996916 | 2269.22449 | 2479.9735 |
| | 871.845571 | 2488.569838 | 1517.47713 | 2722.31576 |
| | 1006.1851 | 1673.504971 | 1707.99971 | 2362.36326 |
| | | 2035.384604 | | 2485.7761 |
| | | 2328.305062 | | 2784.6808 |
| Mean ± SEM | 1312 ± 137.8 | 1895 ± 144.3 | 1916 ± 97.56 | 2445 ± 106.9 |
| Statistical significance (vs. vehicle) | | **p < 0.01 | | **p < 0.01 |

What is claimed is:

1. A method for alleviating or treating demyelinating diseases in a subject, comprising administering to the subject a therapeutically effective amount of a carbamate compound of the following Formula 1, or a pharmaceutically acceptable salt, solvate or hydrate thereof:

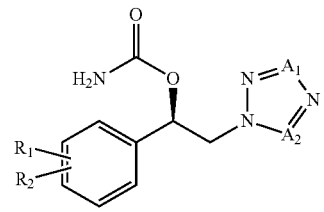

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N,
wherein the demyelinating diseases are one or more selected from the group consisting of multiple sclerosis, Devic's disease, inflammatory demyelinating diseases, central pontine myelinolysis, tabes *dorsalis*, leukoencephalopathies, leukodystrophies, optic neuritis, transverse myelitis, Guillain-Barré syndrome, and Charcot-Marie-Tooth disease.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl)ethyl ester of the following Formula 2:

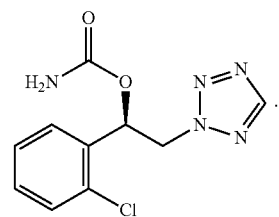

[Formula 2]

4. The method according to claim 1, wherein the method is for the alleviation or treatment of multiple sclerosis.

5. The method according to claim 4, wherein the multiple sclerosis is one or more selected from the group consisting of Clinically isolated syndrome (CIS), Radiologically isolated syndrome (RIS), Clinically definite multiple sclerosis (CDMS), Relapsing remitting multiple sclerosis (RR-MS), Secondary progressive multiple sclerosis (SP-MS), Primary progressive multiple sclerosis (PP-MS) and Progressive relapsing multiple sclerosis (PR-MS).

6. The method according to claim 1, wherein the method is for the alleviation or treatment of optic neuritis.

7. The method according to claim 1, wherein the subject is a mammal.

8. The method according to claim 7, wherein the mammal is a human.

9. The method according to claim 1, wherein the therapeutically effective amount of the carbamate compound of Formula 1 is 50 mg to 500 mg based on the free form.

* * * * *